United States Patent [19]

Edwards

[11] 4,402,952
[45] Sep. 6, 1983

[54] FUNGICIDAL AND INSECTICIDAL 2-THIOHALOALKENYL-4-DIALKOXY-PHOSPHINO-THIOYLOXY-6-ALKYL-1,3-PYRIMIDINES

[76] Inventor: Laroy H. Edwards, 1765 Silverado Trail, Napa, Calif. 94558

[21] Appl. No.: 313,547

[22] Filed: Oct. 22, 1981

[51] Int. Cl.³ .......................... A01N 57/16; C07F 9/65
[52] U.S. Cl. .................................... 424/200; 544/243; 544/299; 544/309
[58] Field of Search ...................... 424/200; 544/243

[56] References Cited

U.S. PATENT DOCUMENTS

| | | | |
|---|---|---|---|
| 2,754,243 | 7/1956 | Gysin et al. | 424/200 |
| 3,657,247 | 4/1972 | Freeman et al. | 544/243 |
| 3,886,156 | 5/1975 | Hofer et al. | 544/243 |

*Primary Examiner*—Mark L. Berch
*Assistant Examiner*—Diana G. Rivers

*Attorney, Agent, or Firm*—D. A. Newell; T. G. DeJonghe; S. L. Biggs

[57] ABSTRACT

2-Thiohaloalkenyl-4-dialkoxyphosphino-thioyloxy-6-alkyl-1,3-pyrimidines represented by the formula:

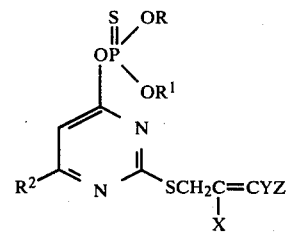

wherein R and $R^1$ are independently lower alkyl; $R^2$ is hydrogen, lower alkyl or lower alkoxy; X, Y and Z are independently halogen or hydrogen with at least one of X, Y and Z being halogen; possess fungicidal and insecticidal activity.

12 Claims, No Drawings

FUNGICIDAL AND INSECTICIDAL 2-THIOHALOALKENYL-4-DIALKOXYPHOS-PHINO-THIOYLOXY-6-ALKYL-1,3-PYRIMIDINES

BACKGROUND OF THE INVENTION

This invention pertains to new fungicidal and insecticidal compounds. With the world now more dependent for food on less and less acreage of land, it is necessary to develop effective insecticides and fungicides to protect crops from insecticidal and fungicidal destruction.

Mayer et al., Chemical Abstracts, Vol. 93 (1980), page 71801t, discloses the synthesis of N,N-dimethyl-O-pyrimidinyl carbamic acid esters. U.S. Pat. No. 2,754,243, issued to Gysin et al. on July 10, 1956, discloses the synthesis and insecticidal activity of 2-thioalkenyl-4-dialkoxyphosphino-thioyloxy-6-alkyl-1,3-pyrimidines by reaction of a thiophosphoric acid diester halide with the appropriately substituted hydroxypyrimidine.

Japanese Pat. No. 55154-986 discloses the synthesis and insecticidal properties of compounds of the formula:

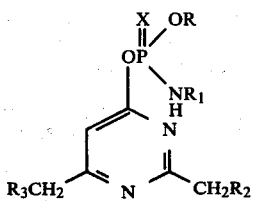

where X is O or S, R is lower alkyl, $R_1$ is lower alkyl, lower alkenyl or lower cyanoalkyl, $R_3$ and $R_2$ are halogen, lower alkoxy, or lower alkylmercapto.

I have now found that the 2-thiohaloalkenyl-4-dialkoxyphosphino-thioyloxy-6-alkyl-1,3-pyrimides of this invention are surprisingly effective as insecticides. Moreover, some of the compounds of this invention are also effective as fungicides.

SUMMARY OF THE INVENTION

The 2-thiohaloalkenyl-4-dialkoxyphosphino-thioyloxy-6-alkyl-1,3-pyrimidines of this invention are represented by the formula:

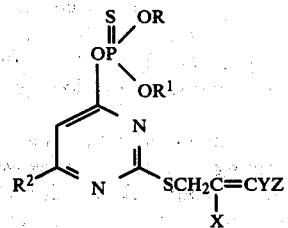

wherein R and $R^1$ are independently lower alkyl; $R^2$ is hydrogen, lower alkyl or lower alkoxy; X, Y and Z are independently halogen or hydrogen with at least one of X, Y or Z being halogen.

I have found that the 2-thiohaloalkenyl-4-dialkoxyphosphino-6-alkyl-1,3-pyrimidines of this invention are particularly effective as fungicides and insecticides. Most surprising was their high degree of effectiveness against Bean Powdery Mildew.

In part due to their superior fungicidal and insecticidal activity, preferred classes of compounds represented by Formula I are those wherein R, $R^1$ and $R^2$ are methyl, ethyl and isopropyl. Preferably, X, Y and Z are independently hydrogen or chlorine with at least one of X, Y or Z being chlorine.

Most preferably, R is methyl and $R^1$ is ethyl.

Representative compounds of this invention include for instance:
2-(1,2-dichloro-3-thioprop-1-enyl)-4-diethoxyphosphino-thioyloxy-1,3-pyrimidine;
2-(1,2-dibromo-3-thioprop-1-enyl)-4-dimethoxyphosphino-thioyloxy-1,3-pyrimidine;
2-(1,2-dichloro-3-thioprop-1-enyl)-4-dimethoxyphosphino-thioyloxy-1,3-pyrimidine;
2-(1,2-dichloro-3-thioprop-1-enyl)-4-diethoxyphosphino-thioyloxy-6-methyl-1,3-pyrimidine;
2-(1,2-dibromo-3-thioprop-1-enyl)-4-diethoxyphosphino-thioyloxy-6-ethyl-1,3-pyrimidine;
2-(1,2-difluoro-3-thioprop-1-enyl)-4-diethoxyphosphino-thioyloxy-6-isopropyl-1,3-pyrimidine;
2-(2-chloro-3-thioprop-1-enyl)-4-diethoxyphosphino-thioyloxy-6-n-hexyl-1,3-pyrimidine;
2-(2-bromo-3-thioprop-1-enyl)-4-diisopropoxyphosphino-thioyloxy-6-n-propyl-1,3-pyrimidine;
2-(1-chloro-3-thioprop-1-enyl)-4-di-n-hexoxyphosphino-thioyloxy-6-methyl-1,3-pyrimidine; and
2-(1-iodo-3-thioprop-1-enyl)-4-dimethoxyphosphino-thioyloxy-6-methyl-1,3-pyrimidine.

DEFINITIONS

As used herein, the following terms have the following meanings, unless expressly stated to the contrary.

The term "phosphino-thioyloxy" refers to the group

The term "dialkoxyphosphino-thioyloxy" refers to the group

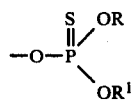

where R and $R^1$ are lower alkyl.

The term "pyrimidine" refers to the group

with the conventional numbering shown.

The term "alkyl" refers to both straight- and branched-chain alkyl groups. The term "lower alkyl" refers to both straight- and branched-chain alkyl groups having a total from 1 through 6 carbon atoms and includes primary, secondary and tertiary alkyl groups. Typical lower alkyls include, for example, methyl, ethyl, n-propyl, isopropyl, n-butyl, t-butyl, n-hexyl, and the like.

The term "alkenyl" refers to unsaturated alkyl groups having a double bond (e.g., $CH_3CH=CH(CH_2)_2—$,)

and includes both straight- and branched-chain alkenyl groups.

"Lower alkenyl" groups refer to alkenyl groups having from 2 through 6 carbon atoms. Typical lower alkenyl groups include, for example, ethylene; but-3-enyl; hex-4-enyl; 2-methylpent-4-enyl; and the like.

The term "alkynyl" refers to unsaturated alkyl groups having a triple bond (e.g., $CH_3C\equiv C(CH_2)_2-$) and includes both straight- and branched-chain alkynyl groups.

The term "lower alkynyl" refers to alkynyl groups having from 2 through 6 carbon atoms and includes, for example, but-3-ynyl; hex-4-ynyl; 3-methylpent-4-ynyl; and the like.

The term "halo or halogen atom" refers to the groups fluoro, chloro, bromo and iodo.

The term "alkoxy" refers to the group $R^1O-$ wherein $R^1$ is alkyl.

The term "lower alkoxy" refers to alkoxy groups having from 1 through 6 carbon atoms and includes, for example, methoxy, ethoxy, t-butoxy, n-hexoxy, and the like.

DETAILED DESCRIPTION OF THE INVENTION

The compounds of this invention can be preferably prepared by reacting 2-thio-4-hydroxy-6-alkyl-1,3-pyrimidine (II) with a substituted 3-chloropropene (III) in accordance with Reaction (1), followed by treatment of the recovered product with dialkyloxyphosphino-thioyloxychloride (V) as shown in Reaction (2):

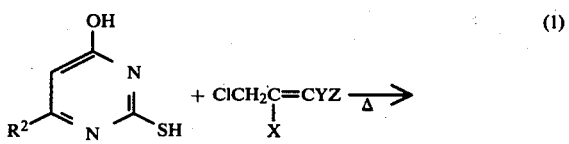

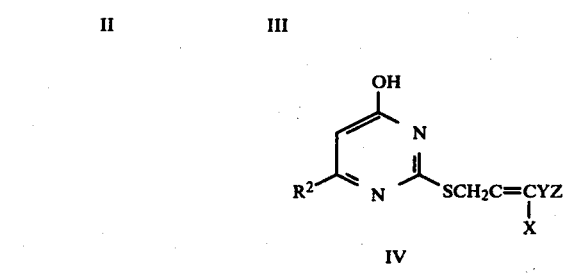

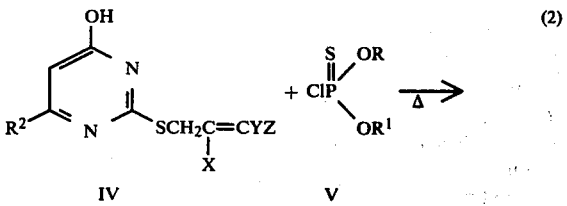

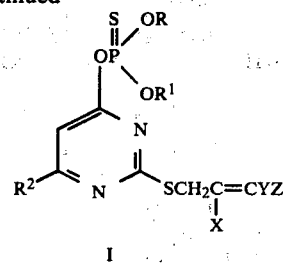

where X, Y, Z, R, $R^1$ and $R^2$ are as defined above. Reaction (1) can be conducted by reacting substantially equimolar amounts of II and III. The reaction is conducted in the liquid phase using an organic solvent such as ethanol, acetone, dimethyoxyethane, dimethylformamide, methanol, and the like. The system is treated with between 1 to 2 equivalents of an organic or inorganic base. The preferred base is an inorganic base such as potassium carbonate, potassium bicarbonate or sodium hydride. Preferred conditions for Reaction (1) are using potassium carbonate as the base and ethanol as the solvent. Reaction pressure is not critical and for convenience, the reaction pressure is generally atmospheric. The reaction is generally heated at reflux and is completed in 1 to 24 hours. The 2-thiohaloalkenyl-4-hydroxy-6-alkyl-1,3-pyrimidine, product (I), is isolated by conventional procedures such as extraction, filtration, chromatography, distillation, or alternatively, is used directly in Reaction (2) without purification and/or isolation.

In Reaction (2), the 2-thiohaloalkenyl-4-hydroxy-6-alkyl-1,3-pyrimidine (IV) is treated with a substantially equimolar amount of dialkoxy phosphorochloridothionate (V). The reaction is conducted in the liquid phase using an organic solvent such as ethanol, acetone, dimethoxyethane, dimethylformamide, methanol, and the like. The reaction solution is treated with between 1 to 2 equivalents of an organic or inorganic base. The preferred base is an inorganic base such as potassium carbonate, potassium bicarbonate or sodium hydride. Preferred reaction conditions are using potassium carbonate in an acetone medium. Reaction pressure is not critical. For convenience, the reaction pressure is generally atmospheric. The reaction is generally heated at reflux and is completed in 1 to 24 hours. The 2-thiohaloalkenyl-4-dialkoxyphosphino-thioyloxy-6-alkyl-1,3-pyrimidine compound is isolated by conventional procedures such as extraction, filtration, chromatography, or distillation.

Alternatively, the compounds of this invention can be prepared by reacting 2-thio-4-hydroxy-6-alkyl-1,3-pyrimidine (II) with a multi-halosubstituted 1-chloropropane using 2 equivalents of an inorganic or organic base. The scheme for this procedure is shown in Reaction (4) below:

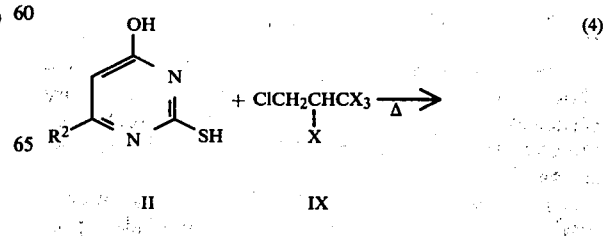

-continued

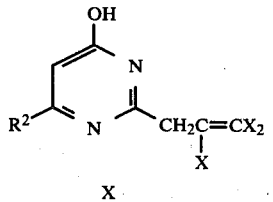

where $R^2$ is as defined above and X may be either hydrogen or halogen but at least one of X must be halogen. Reaction (4) can be conducted by reacting substantially equimolar amounts of II and IX. The reaction is conducted in the liquid phase using an organic solvent such as ethanol, acetone, dimethoxyethane, dimethylformamide, methanol, and the like. The reaction requires 2 equivalents of an inorganic or organic base. The preferred base is an inorganic base such as potassium carbonate, potassium bicarbonate, or sodium hydride. Preferred reaction conditions are using potassium carbonate in acetone. The intermediate X is then converted to the product VII as described above.

UTILITY

The compounds of the invention are useful for controlling fungi, particularly leaf blights caused by organisms such as *Phytophthora infestans conidia,* and *Septoria apii,* powdery mildew caused by organisms such as *Plasmopara viticola* and *Erysiphe polygori conidia,* and other fungal infections. However, some funicidal compounds of the invention may be more fungicidally active than others against particular pests.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifible concentrates, as solutions, or as any of several other known types of formulations, depending on the desired mode of application.

Wettable powders are in the form of finely divided particles which disperse readily in water or other dispersant. These compositions normally contain from about 5% to 80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents, include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emusifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant growth regulators, fertilizers, etc.

The compounds of the invention are also useful as insecticides, particularly against such insects as aphids (*Aphis gossypii* Glover), cabbage looper (*Trichophisia ni*), rootworm (*Diabroctia larvae*) and mosquito larvae (*Aedis aegypti*). However, some insecticidal compounds of the invention may be more insecticidally active than others against particular pests.

Like most insecticides, they are not usually applied full strength, but are generally incorporated with conventional biologically inert extenders or carriers normally employed for facilitating dispersion of active ingredients for agricultural chemical applications, recognizing the accepted fact that the formulation and mode of application may affect the activity of a material. The toxicants of this invention may be applied as sprays, dusts, or granules to the insects, their environment or hosts susceptible to insect attack. They may be formulated as granules of large particle size, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from 5% to 80% toxicant and the rest inert material which includes dispersing agents, emulsifying agents, and wetting agents. The powder may be applied to the soil as a dry dust or preferably as a suspension in water. Typical carriers include fuller's earth, kaolin clays, silicas, and other highly absorbent, readily wet, inorganic diluents. Typical wetting, dispersing, or emulsifying agents used in insecticidal formulations include, for example, the alkyl and alkylaryl sulfonates and sulfonates and their sodium salts; alkylamide sulfonates, including fatty methyl taurides; alkylaryl polyether alcohols, sulfated higher alcohols, and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the pesticidal composition.

Dusts are freely flowing admixtures of the active ingredient with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about fifty microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the toxicant with a liquid or solid emulsifying agent, or may also contain a liquid carrier, such as xylene, heavy aromatic naphthas, isophorone, and other non-volatile organic solvents. For application, these concentrates are dispersed in water or other liquid carrier, and normally applied as a spray to the area to be treated.

Other useful formulations for insecticidal applications include simple solutions of the active ingredient in a dispersant in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover-crop canopy. Baits, prepared by mixing solid or liquid concentrates of the toxicant with a suitable food, such as a mixture of cornmeal and sugar, are useful formulations for control of insect pests. Pressurized sprays, typically aerosols wherein the active ingredient is dispersed in finely divided form as a result of vaporization of a low-boiling dispersant solvent carrier, such as the Freons, may also be used. All of these techniques for formulating and applying the active ingredient are well known in the art.

The percentages by weight of the toxicant may vary according to the manner in which the composition is to be applied and the particular type of formulation, but in general comprises 0.1% to 95% of the toxicant by weight of the insecticidal composition.

The insecticidal compositions may be formulated and applied with other active ingredients, including nematocides, insecticides, fungicides, bactericides, plant growth regulators, fertilizers, etc. In applying the chemical an effective amount and concentration of the toxicants of this invention is, of course, employed.

The terms "insecticide" and "insect" as used herein refer to their broad and commonly understood usage rather than to those creatures which in the strict biological sense are classified as insects. Thus, the term "insect" is used not only to include small invertebrate animals belonging to the class "Insecta," but also to other related classes of arthropods, whose members are segmented invertebrates having more or fewer than six legs, such as spiders, mites, ticks, centipedes, worms, and the like.

A further understanding of the invention can be had on the following non-limiting Examples. Wherein, unless expressly stated to the contrary, all temperatures and temperature ranges refer to the centigrade system and the term "ambient" or "room temperature" refers to about 20° to 25° C. The term "percent" refers to weight percent and the term "mol" or "mols" refers to gram mols. The term "equivalent" refers to a quantity of reagent equal in mols to the mols of the preceding or succeeding reactant recited in that example in terms of finite mols or finite weight or volume. Also, unless expressly stated to the contrary, resulting mixtures, where applicable, of E and Z isomers in the compounds were not separated. Also, geometric isomer and racemic mixtures are used as starting materials and correspondingly isomer mixtures are obtained as products.

EXAMPLE 1

Preparation of 2-(2-chloro-3-thio-prop-1-enyl)-4-hydroxy-6-methyl-1,3-pyrimidine 2-Thio-4-hydroxy-6-methyl-1,3-pyrimidine, 42.6 g, was added to 33.2 g of 2,3-dichloro-prop-1-ene and 20.7 g potassium carbonate in 400 ml of ethanol. The system was heated at reflux for 8 hours. The ethanol was removed by stripping and the residue washed with water. The residue was dissolved in dichloromethane and dried with magnesium sulfate. The dichloromethane was removed by stripping to give 35 g of the 2-(2-chloro-3-thio-prop-1-enyl)-4-hydroxy-6-methyl-1,3-pyrimidine. The product was a white solid, m.p. 146° to 148° C.

Examination by NMR spectroscopy was in complete accord with the proposed structure.

EXAMPLE 2

Preparation of 2-(1,1-dichloro-3-thio-prop-1-enyl)-4-hydroxy-6-methyl-1,3-pyrimidine 2-Thio-4-hydroxy-6-methyl-1,3-pyrimidine, 50 g, was added to 64.0 g of 1,1,1,3-tetrachloropropane and 48.3 g of potassium carbonate in 400 ml of ethanol. The system was heated at reflux for 8 hours. The ethanol was removed by stripping and the residue washed with water. The residue was dissolved in dichloromethane and dried with magnesium sulfate. The dichloromethane was removed by stripping to give 55 g of the 2-(1,1-dichloro-3-thio-prop-1-enyl)-4-hydroxy-6-methyl-1,3-pyrimidine.

Examination by NMR spectroscopy was in complete accord with the proposed structure.

EXAMPLE 3

Preparation of 2-(3-thio-prop-1-ynyl)-4-hydroxy-6-methyl-1,3-pyrimidine

2-Thio-4-hydroxy-6-methyl-1,3-pyrimidine, 50 g, was added to 300 ml of dimethoxyethane. 11.8 g sodium hydride was added slowly over a period of time. The resulting solution was heated at reflux for 1½ hours and then cooled to room temperature. 50 g of 3-bromopropyne was added and the solution was heated at reflux for 1½ hours and then at room temperature for 14 hours. The reaction solution was washed with water, filtered and the product extracted with dichloromethane. The dichloromethane was stripped to give a white solid, m.p. 164° to 166° C.

Examination by NMR and IR spectroscopy was in complete accord with the proposed structure.

EXAMPLE 4

Preparation of 2-(3-thio-propa-1,2-dienyl)-4-hydroxy-6-methyl-1,3-pyrimidine

2-Thio-4-hydroxy-6-methyl-1,3-pyrimidine, 75 g, was added to 75.6 g of propargyl bromide and 41 g of potassium carbonate in 600 ml ethanol. The system was stirred at reflux for 8 hours and then at room temperature for an additional 14 hours. The system was then filtered and the ethanol removed by stripping. The residue was washed with water and the product extracted with dichloromethane. The organic solution was dried with magnesium sulfate and the dichloromethane removed by stripping to give a mixture of the 2-(3-thio-propa-1,2-dienyl)-4-hydroxy-6-methyl-1,3-pyrimidine and the 2-(3-thio-prop-1-ynyl)-4-hydroxy-6-methyl-1,3-pyrimidine. Column chromatography over silica gave 15 g of the allene compound, m.p. 108° to 110° C.

Examination by IR and NMR spectroscopy was in complete accord with the proposed structure.

EXAMPLE 5

Preparation of 2-(2-chloro-3-thio-prop-1-enyl)-4-diethoxyphosphinothioyloxy-6-methyl-1,3-pyrimidine 2-(3-Thio-2-chloro-prop-1-enyl)-4-hydroxy-6-methyl-1,3-pyrimidine, 10 g, and 7.7 g potassium carbonate was added to acetone. The system was refluxed for 2 hours and then cooled to room temperature. After cooling, 10.4 g of diethoxy phosphorochloridothionate was added. The system was again refluxed for 7 hours and then stirred at room temperature for an additional 15 hours. The solution was then filtered and the acetone removed by stripping. The residue was washed with water. The product was extracted with dichloromethane and dried with magnesium sulfate. The dichloromethane was removed by stripping, to give, after chromatography, the 2-(3-thio-2-chloro-prop-1-enyl)-4-diethoxyphosphino-thioyloxy-6-methyl-1,3-pyrimidine, which is Compound #2 in Table 1.

EXAMPLE 6

Preparation of 2-(1,2-dichloro-3-thio-prop-1-enyl)-4-diethoxyphosphino-thioyloxy-1,3-pyrimidine 2-(1,2-Dichloro-3-thio-prop-1-enyl)-4-hydroxy-1,3-pyrimidine, 9.5 g, was added to 250 ml dimethoxyethane. 1.4 g sodium hydride was slowly added to the system. After addition, the system was heated for 1 hour and then cooled to room temperature. After cooling, 6.4 g of diethoxy phosphorochloridothionate was added. The system was refluxed for 4½ hours and then stirred at room temperature for 14 hours. The reaction was stopped and the reaction solution poured into water. The product was extracted with dichloromethane and the organic solution dried with magnesium sulfate. The dichloromethane was removed by stripping. The residue was purified by chromatography to give 3.0 g of 2-(1,2-dichloro-3-thio-prop-1-enyl)-4-diethoxyphosphino-thioyloxy-1,3-pyrimidine.

Examination by IR and NMR spectroscopy was in complete accord with the proposed structure.

EXAMPLE 7

Grape Downy Mildew Control

The compounds of the invention were tested for the control of Grape Downy Mildew organism *Plasmopara viticola*. Detached leaves, between 70 mm and 85 mm in diameter, of 7-week-old *Vitis vinifera cultivar* Emperor grape seedlings were used as hosts. The leaves were sprayed with a solution of the test compound in acetone. The sprayed leaves were dried, inoculated with a spore suspension of the organism, placed in a humid environmental chamber and incubated at 66° to 68° F. and about 100% relative humidity. After incubation for two days, the plants were then held in a greenhouse for seven to nine days; then the amount of disease control was determined. The percent disease control provided by a given test compound was based on the percent disease reduction to untreated check plants. The results are tabulated in Table 5.

EXAMPLE 8

Bean Powdery Mildew

The compounds of the invention were tested for the control of the Bean Powdery Mildew organism *E. polygoni conidia*. Seedling bean plants were sprayed with a 250-ppm solution of the test compound in acetone, water and a nonionic emulsifier. The sprayed plants were then inoculated 1 day later with the organism. The plants were allowed to dry and were maintained for 10 days at temperatures of 68° F. at night with daytime temperatures of 72° to 80° F.; relative humidity was maintained at 40% to 60%. The percent disease control provided by a given test compound was based on the percent disease reduction relative to the untreated check plants. The results are tabulated in Table 5.

EXAMPLE 9

Tomato Late Blight

Compounds of the invention were tested for the control of the Tomato Late Blight organism *Phytophthora infestans conidia*. Five- to six-week-old tomato (variety Bonny Best) seedlings were used. The tomato plants were sprayed with a 250-ppm solution of the test compound in acetone, water and a small amount of a nonionic emulsifier. The sprayed plants were then inoculated 1 day later with the organism, placed in an environmental chamber and incubated at 66° to 68° F. and 100% relative humidity for at least 16 hours. Following the incubation, the plants were allowed to dry and then were maintained in a greenhouse for approximately 7 days. The percent disease control provided by a given test compound was based on the percent disease reduction relative to untreated check plants. The compounds giving effective control at the test concentration are tabulated in Table 5.

EXAMPLE 10

Celery Late Blight

Compounds of the invention were tested for the control of Celery Late Blight using celery (Utah) plants 11 weeks old. The Celery Late Blight organism was *Septoria apii*. The celery plants were sprayed with solutions of the candidate toxicant mixed with acetone, water and a nonionic emulsifier. The plants were then inoculated with the organism and placed in an environmental chamber and incubated at 66° to 68° F. in 100% relative humidity for an extended period of time (approximately 48 hours). Following the incubation, the plants were allowed to dry and then were maintained in a greenhouse for approximately 14 days. The percent disease control provided by a given candidate toxicant is based on the percent disease reduction relative to untreated check plants. The compounds giving effective control at the test concentrations are reported in Table 5.

EXAMPLE 11

Aphid Control

The compounds of the invention were tested for their insecticidal activity against cotton aphids (*Aphis gossypii* Glover). An acetone solution of the candidate toxicant containing a small amount of nonionic emulsifier was diluted with water to 40 ppm. Cucumber leaves infested with the cotton aphids were dipped in the toxicant solution. Mortality readings were taken after 24 hours. The results are tabulated in Table 6.

EXAMPLE 12

Cabbage Looper Control

The compounds of the invention were tested for their insecticidal activity against Cabbage Looper (*Trichophisia ni*). An acetone solution of the candidate toxicant containing a small amount of nonionic emulsifier was diluted with water to 500 ppm. Excised cucumber leaves were dipped in the toxicant solution and allowed to dry. They were then infested with Cabbage Looper larvae. Mortality readings were taken after 24 hours. The results are tabulated in Table 6.

EXAMPLE 13

Rootworm Control

The compounds of the invention were tested for control of Corn Rootworm (Diabroctia larvae). A batch of 20 to 30 two-day-old Diabroctia eggs was placed on the bottom of a 237-cc clear plastic cup. These eggs were then covered with about 45 cc of soil containing 15 ppm of the test compound. The soil is watered with 15 cc of water. The corn seeds, presoaked for 2 hours, were evenly distributed on the soil surface. Then an additional 45 cc of the same treated soil was added to cover the seeds, and this soil was watered with an additional 15 cc of water. The test cup was kept at 70° F. with occasional light watering just to keep the soil damp.

After 14 to 16 days, the test unit was examined under a dissecting scope, by observing the corn roots and larvae through the cup's clear plastic walls. Control of newly hatched larvae was rated by visually evaluating the degree of corn root damage by feeding larvae in conjunction with the physical presence of live and/or dead larvae. The results are tabulated in Table 6.

EXAMPLE 14

Control of Mosquito Larvae

The compounds of the invention were tested for control of Mosquito Larvae (*Aedis aegypti*). A plastic cup was first filled with 90 ml deionized water and then infested with early 4th-stage Mosquito Larvae contained in 10 ml water. One rabbit food pellet was added to the cup to provide food for the larvae. 20 Microliters of a 500-ppm solution of the toxicant were added to the cup. The water was then thoroughly mixed to give a 0.1-ppm solution of the toxicant. The test cup was covered with a plastic lid in order to prevent evaporation and to confine subsequent emerging adults. The test unit was held at 27° C. for 6 days. Mortality readings were then taken. The results for the test compounds are given in Table 6.

TABLE 1

Compounds of the formula:

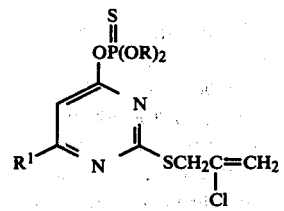

| Compound # | R | R¹ | C calc. | C found | H calc. | H found | N calc. | N found | |
|---|---|---|---|---|---|---|---|---|---|
| 1 | $CH_3$ | $CH_3$ | 35.24 | 37.09 | 4.14 | 4.71 | 8.22 | 8.36 | oil |
| 2 | $C_2H_5$ | $CH_3$ | 39.08 | 42.28 | 4.92 | 5.74 | 7.59 | 7.11 | oil |
| 3 | $CH_3$ | H | 33.08 | 36.71 | 3.70 | 4.25 | 8.57 | 9.19 | oil |
| 4 | $C_2H_5$ | H | 37.23 | 38.47 | 4.54 | 5.12 | 7.90 | 7.89 | oil |
| 5 | $CH_3$ | $n\text{-}C_3H_7$ | 39.08 | 41.40 | 4.92 | 5.38 | 7.59 | 8.35 | oil |

TABLE 1-continued

Compounds of the formula:

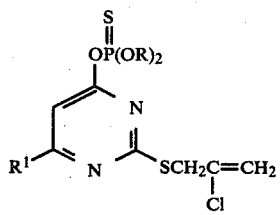

| Compound # | R | R$^1$ | C calc. | C found | H calc. | H found | N calc. | N found | |
|---|---|---|---|---|---|---|---|---|---|
| 6 | C$_2$H$_5$ | n-C$_3$H$_7$ | 42.37 | 42.56 | 5.59 | 5.89 | 7.06 | 7.05 | oil |

TABLE 2

Compounds of the formula:

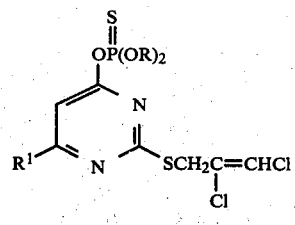

| Compound # | R | R$^1$ | C calc. | C found | H calc. | H found | N calc. | N found | |
|---|---|---|---|---|---|---|---|---|---|
| 7 | CH$_3$ | CH$_3$ | 32.01 | 33.50 | 3.49 | 3.38 | 7.47 | 8.01 | oil |
| 8 | C$_2$H$_5$ | CH$_3$ | 35.74 | 38.71 | 4.25 | 4.51 | 6.95 | 7.01 | oil |
| 9 | CH$_3$ | H | 29.93 | 31.10 | 3.07 | 3.40 | 7.76 | 7.88 | oil |
| 10 | C$_2$H$_5$ | H | 33.94 | 33.45 | 3.88 | 3.63 | 7.20 | 7.22 | oil |
| 11 | C$_2$H$_5$ | n-C$_3$H$_7$ | 38.98 | 39.52 | 4.91 | 5.49 | 6.49 | 6.15 | oil |

TABLE 3

Compounds of the formula:

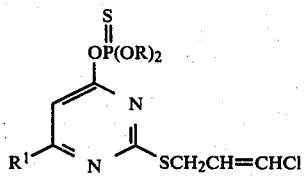

| Compound # | R | R$^1$ | C calc. | C found | H calc. | H found | N calc. | N found | |
|---|---|---|---|---|---|---|---|---|---|
| 12 | CH$_3$ | CH$_3$ | 35.24 | 37.02 | 4.14 | 4.52 | 8.22 | 8.74 | oil |
| 13 | C$_2$H$_5$ | CH$_3$ | 39.08 | 41.85 | 4.92 | 6.11 | 7.6 | 8.1 | oil |
| 14 | C$_2$H$_5$ | H | 37.23 | 37.46 | 4.54 | 4.85 | 7.90 | 7.18 | oil |
| 15 | CH$_3$ | H | 33.08 | 34.64 | 3.7 | 3.9 | 8.57 | 9.15 | oil |
| 16 | CH$_3$ | n-C$_3$H$_7$ | 39.07 | 37.94 | 4.92 | 4.84 | 7.59 | 7.20 | oil |
| 17 | C$_2$H$_5$ | n-C$_3$H$_7$ | 42.37 | 43.56 | 5.59 | 5.98 | 7.06 | 7.28 | oil |

TABLE 4

Compounds of the formula:

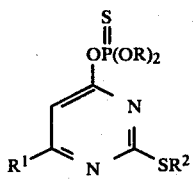

| Compound # | R | R$^1$ | C calc. | C found | H calc. | H found | N calc. | N found | | R$^2$ |
|---|---|---|---|---|---|---|---|---|---|---|
| 18 | C$_2$H$_5$ | CH$_3$ | 35.74 | 35.30 | 4.25 | 4.22 | 6.95 | 7.05 | oil | $-CH_2CH=C\begin{smallmatrix}Cl\\Cl\end{smallmatrix}$ |
| 19 | C$_2$H$_5$ | CH$_3$ | 43.36 | 41.58 | 5.15 | 5.40 | 8.43 | 7.97 | oil | $-CH_2C{\equiv}CH$ |

TABLE 5

Fungicidal Activity

| Compound No. | Grape Downy Mildew | Tomato Late Blight | Celery Late Blight | Bean Powdery Mildew |
|---|---|---|---|---|
| 1 | 8 | 0 | — | 77 |
| 2 | 0 | 14 | — | 98 |
| 3 | 29 | 0 | 0 | 21 |
| 4 | 0 | 0 | 14 | 21 |
| 5 | 0 | — | 51 | 0 |
| 6 | 44 | 0 | 23 | 0 |
| 7 | 0 | 6 | 14 | 100 |
| 8 | 18 | 6 | 0 | 100 |
| 9 | 14 | 0 | 14 | 39 |
| 10 | 13 | 18 | 21 | 69 |
| 11 | 0 | 0 | — | 0 |
| 12 | 99 | 44 | 0 | 0 |
| 13 | 54 | 0 | 0 | 0 |
| 14 | 0 | 0 | 0 | 0 |
| 15 | 35 | 0 | 0 | 0 |
| 16 | 8 | 18 | 37 | 0 |
| 17 | 0 | 35 | 37 | 14 |
| 18 | 57 | 0 | 14 | 28 |
| 19 | 0 | 18 | — | 0 |

TABLE 6

Insecticidal Activity

| Compound No. | Aphid (40 ppm) | Rootworm (15 ppm) | Cabbage Looper (500 ppm) | Mosquito Larvae (0.1 ppm) |
|---|---|---|---|---|
| 1 | 99 | — | 0 | 100 |
| 2 | 99 | — | 10 | 0 |
| 3 | 100 | — | 0 | 100 |
| 4 | 100 | — | 10 | 100 |
| 5 | 0 | 0 | 0 | 0 |
| 6 | 99 | 0 | 0 | 0 |
| 7 | 90 | — | 0 | 100 |
| 8 | 99 | — | 0 | 0 |
| 9 | 99 | — | 0 | 100 |
| 10 | 100 | — | 10$^1$ | — |
| 11 | 99 | 94 | 0 | 80 |
| 12 | 98 | — | 0 | 100 |
| 13 | 99 | — | 0 | 0 |
| 14 | 100 | 100 | 60$^2$ | 100 |
| 15 | 100 | — | 0 | 100 |
| 16 | 60 | — | 0 | 100 |
| 17 | 90 | — | 0 | 0 |
| 18 | 100 | — | 0 | 70 |
| 19 | 100 | — | 0 | 0 |

$^1$50% at 7 days
$^2$100% at 14 days

I claim:

1. A compound of the formula:

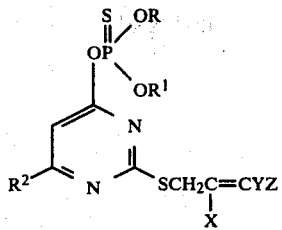

wherein R and R$^1$ are independently lower alkyl; R$^2$ is hydrogen, lower alkyl or lower alkoxy; and X, Y and Z are independently hydrogen or halogen atoms with at least one of X, Y and Z being halogen.

2. A compound according to claim 1 wherein X is chloro.

3. A compound according to claim 2 wherein Y is hydrogen and Z is chloro.

4. The compound according to claim 3 wherein R and R$^1$ are ethyl and R$^2$ is methyl.

5. A method of controlling fungi comprising contacting said fungi or their growth environment with a fungicidally effective amount of a compound of the formula defined in claim 1 with the proviso that when R and R$^1$ are ethyl, X and Z are chloro and Y is hydrogen, R$^2$ is not n-propyl; and with the further proviso that when R and R$^1$ are ethyl, Z is chloro and X and Y are hydrogen, R$^2$ is not hydrogen.

6. A method according to claim 5 wherein said fungi is Bean Powdery Mildew.

7. A method of controlling fungi comprising contacting said fungi or their growth environment with a fungicidally effective amount of a compound of the formula defined in claim 4.

8. A method according to claim 7 wherein said fungi is Bean Powdery Mildew.

9. A fungicidal composition comprising a biologically inert carrier and a fungicidally effective amount of a compound of the formula defined in claim 1 with the proviso that when R and R$^1$ are ethyl, X and Z are chloro and Y is hydrogen, R$^2$ is not n-propyl; and with the further proviso that when R and R$^1$ are ethyl, Z is chloro and X and Y are hydrogen, R$^2$ is not hydrogen.

10. A fungicidal composition comprising a biologically inert carrier and a fungicidally effective amount of a compound of the formula defined in claim 4.

11. A method of killing insects comprising contacting said insects or their habitat with an insecticidally effective amount of a compound of the formula defined in claim 1 with the proviso that when X is chloro, Y and Z are hydrogen and R and $R^1$ are methyl, $R^2$ is not n-propyl.

12. An insecticidal composition comprising a biologically inert carrier and an insecticidally effective amount of a compound of the formula defined in claim 1 with the proviso that when X is chloro, Y and Z are hydrogen and R and $R^1$ are methyl, $R^2$ is not n-propyl.

* * * * *